United States Patent [19]

Matsumoto et al.

[11] Patent Number: 4,745,217
[45] Date of Patent: May 17, 1988

[54] PROCESS FOR PRODUCING METHACRYLIC ACID

[75] Inventors: Mutsumi Matsumoto; Hideki Sugi, both of Takasaki; Atsushi Sudo, Annaka, all of Japan

[73] Assignee: Nippon Kayaku Kabushiki Kaisha, Tokyo, Japan

[21] Appl. No.: 484,610

[22] Filed: May 26, 1983

Related U.S. Application Data

[60] Continuation of Ser. No. 239,409, Mar. 2, 1982, abandoned, which is a division of Ser. No. 948,761, Oct. 5, 1978, Pat. No. 4,273,676.

[30] Foreign Application Priority Data

Oct. 31, 1977 [JP] Japan ................... 52-129685

[51] Int. Cl.$^4$ ............... C07C 51/25; C07C 57/055
[52] U.S. Cl. ............................. 562/534; 502/209; 562/535
[58] Field of Search .............. 562/534, 535; 502/209

[56] References Cited

U.S. PATENT DOCUMENTS 4,115,441 9/1978 Shaw et al. ................. 562/535
4,180,678 12/1979 Wada et al. ................. 562/535

*Primary Examiner*—Vivian Garner
*Attorney, Agent, or Firm*—Henry C. Nields

[57] ABSTRACT

A catalyst having a heteropoly-acid structure and the general formula:

$$Mo_aV_bP_cCu_dX_eO_f$$

wherein Mo, V, P, Cu and O represent respectively molybdenum, vanadium, phosphorus, copper and oxygen, X represents one or more elements selected from the group consisting of tin, thorium, germanium, nickel, iron, cobalt, magnesium, zinc, titanium, lead, rhenium, zirconium, and chromium, and a, b, c, d, e and f represent the atomic ratio of the elements where, a is 10
b is a number of 3 or less than 3 excluding 0,
c is a number of 0.5 to 3,
d is a number of 3 or less than 3 excluding 0,
e is a number of 3 or less than 3 excluding 0,
f is a number determined depending on the valency and atomic ratio of other elements.

There is also provided a process for producing methacrylic acid by oxidizing methacrolein with molecular oxygen or molecular oxygen-containing gas in the presence of the catalyst defined above.

5 Claims, No Drawings

PROCESS FOR PRODUCING METHACRYLIC ACID

This application is a continuation of application Ser. No. 239,409, filed Mar. 2, 1982, now abandoned, which is a divisional application of Ser. No. 948,761, filed Oct. 5, 1978, now U.S. Pat. No. 4,273,676.

DETAILED DESCRIPTION OF THE INVENTION

This invention relates to a process for producing methacrylic acid by the oxidation of methacrolein characterized by the use of a new catalyst which has a high activity, selectivity, as well as very long catalyst life.

This invention relates as well to the catalyst therefor.

Although various catalyst systems have recently been proposed for the catalytic oxidation of methacrolein in gas phase, industrial practice for the oxidation of methacrolein has not yet been attained in contrast to the oxidation of acrolein for the production of acrylic acid. The difficulty arises, it is considered, from the facts that yields of the end products are not so high as those in the production of acrylic acid, the life of the catalyst is too short to maintain a stable catalytic activity for a long time and the like.

Most of the catalysts for the catalytic oxidation of methacrolein in gas phase proposed so far comprise a molybdenum-phosphorus system as a basic component and have a structure of a heteropoly-acid salt composed basically of phosphomolybdate such as of an ammonium salt and an alkali metal salt.

However, phosphomolybdic acid or its ammonium or alkali metal salt-based catalyst has a serious disadvantage that the catalyst life is short. During continuous reaction for a long time, gradual decomposition of phosphomolybdic acid or its ammonium or alkali metal salt structure and crystal growth of molybdenum trioxide are found through X-ray diffraction or the like accompanied by the reduction in the catalytic activity. Consequently, most of the catalysts proposed so far do not have a sufficient catalyst life for industrial use and thus very mild reaction conditions are required in order to maintain long life catalytic activity in the catalyst system. This is far from satisfying economic requirements at present.

In view of low selectivity, low activity and short life of the conventional catalysts for catalytic gas phase oxidation of methacrolein, the inventors of the present application have made an earnest study on eliminating the defects of the catalyst in the industrial use and accomplished the invention on the discovery that a novel catalyst according to this invention can produce methacrylic acid from methacrolein at a high yield and in a stabilized state for a long time.

This invention relates to a process for producing methacrylic acid by oxidizing methacrolein with molecular oxygen or molecular oxygen-containing gas characterized by the use of a catalyst having a heteropoly-acid structure and the general formula:

$$Mo_aV_bP_cCu_dX_eO_f$$

wherein Mo, V, P, Cu and O represent respectively molybdenum, vanadium, phosphorus, copper and oxygen, X represents one or more elements selected from the group consisting of tin, thorium, germanium, nickel, iron, cobalt, magnesium, zinc, titanium, lead, rhenium, zirconium, and chromium. and a, b, c, d, e and f represent the atomic ratio of the elements where, a is 10, b is a number of 3 or less than 3 excluding 0 and, preferably, 0.5 to 2, c is a number of 0.5 to 3 and, preferably, 0.5 to 2, d is a number of 3 or less than 3 excluding 0 and, preferably, 0.01 to 1, e is a number of 3 or less than 3 excluding 0 and, preferably, 0.01 to 0.5, f is a number determined depending on the valency and atomic ratio of other elements and is usually a number of 32 to 80.

This invention relates as well to the catalyst defined above.

Particularly preferred component X includes tin, thorium, germanium, nickel, iron, cobalt, titanium and zirconium.

The foregoing catalyst used in this invention contains various elements and has a heteropolyacid structure as shown by the characteristic peaks at $2\theta = 8.0°$, $8.9°$, $9.3°$ and the like when observed in X-ray diffraction. While the basic structure of the catalyst is a phosphovanadomolybdic acid, other elements incorporated therein are considered to contribute to the improvements in the catalytic activity and selectivity, as well as in the stability of the structure by partially replacing the constituent elements in the phosphovanadomolybdic acid and being incorporated into the structure of the heteropoly-acid.

The catalyst of this invention is water soluble since it has a heteropoly-acid structure as described above. It may additionally contain water insoluble components such as oxides of the consituent elements but they have no substantial effects on the performance of the catalyst of this invention.

It is considered that, as in the conventional case, the catalyst of this invention is also in the reduced form under the reaction conditions by being reduced with the feed gas containing methacrolein at the early stage of the reaction. The reduced form can be obtained also by using a reducible starting material for the constituent elements of the catalyst, adding the reductant when preparing the catalyst or treating the catalyst with a reducible gas.

The catalyst of this invention is excellent for the industrial use since it has a high activity, a high selectivity, as well as very long catalyst life. Further, according to this invention, the reaction can be conducted at a high space velocity, because the increase in the space velocity has no substantial effects on the results of the reaction where the catalyst of this invention is employed. The catalyst of this invention is water soluble, which provides advantages in that it can easily be carried on a carrier and regenerated also with ease by dissolving it again in water after being deactivated in a long use for the reaction.

While the catalyst of this invention can be prepared by general methods for preparing usual heteropoly-acids, it should particularly be noted to avoid the formation of a heteropoly-acid ammonium salt structure in the resultant catalyst.

The catalyst of this invention can be prepared, for example, in the following manner. A heteropoly-acid containing phosphorus element as a central atom can easily be synthesized as conventionally utilized in a quantitative or qualitative analysis for various elements. Accordingly, the catalyst of this invention can also be prepared by reacting the starting materials for the constituent elements in water or in an organic solvent, converting the reaction product into the corresponding acid when it is ammonium salt, extracting the reaction product if necessary, and evaporating to dryness. The conversion of ammonium salt into the corresponding acid can be carried out through conventional ways, for example, by ether extraction from an acidic aqueous solution, ion exchange process and the like. The extraction of the reaction product can be carried out by using a suitable organic solvent such as ether.

Particularly preferred preparation methods include those such as dispersing or dissolving the starting material, for example, oxides or phosphates of the constituent elements into water, reacting the same under heating while optionally adding hydrogen peroxide, removing insoluble component if necessary, and then evaporating the solution to dry, or reacting phosphovanadomolybdic acid with oxides, phosphates, sulfates and the likes of other constituent elements.

Various substances can be used as the starting material for the constituent elements of the catalyst, so long as they are treated in such a process as resulting in a catalyst of a heteropoly-acid structure but not of a ammonium salt structure.

The starting materials usable for the molybdenum component include, for example, molybdenum trioxide, molybdic acid or its salt, heteromolybdic acid or its salts, molybdenum metal and the like.

The starting materials usable for the phosphorus component include orthophosphoric acid, phosphorus acid, hypophosphorous acid or the salts thereof, phosphorus pentoxide and the like.

The starting materials usable for the vanadium component include vanadium pentoxide, vanadium oxalate, vanadium sulfate, vanadic acid or its salts, vanadium metal and the like.

The starting materials usable for the copper component include copper oxide, copper phosphate, copper sulfate, copper nitrate, copper molybdate, copper metal and the like.

The starting materials usable for the component X include corresponding oxides, phosphates, nitrates, sulfates, carbonates, molybdates, metals of the elements X and the like.

While the catalyst according to this invention exhibits a high catalytic activity as it is, preferable effects such as improvements in thermal stability and catalyst life and increase in yield of methacrylic acid can be expected by carrying it on a suitable carrier. Preferred carriers include silicon carbide, $\alpha$-alumina, aluminum powder, diatomaceous earth, titanium oxide and the like. The active carriers which react with heteropoly-acid are not preferable.

The calcination process which is required in numerous cases is not required when preparing the catalyst of this invention. Therefore, the catalyst of this invention can be prepared with ease and the price of the catalyst can be reduced.

The reactants used for the oxidizing reaction in this invention are methacrolein and molecular oxygen or molecular oxygen-containing gas, wherein the molar ratio of oxygen to methacrolein preferably lies between 0.5 and 10 and, more preferably, between 2 and 5.

It is preferable for smoothly proceeding the reaction to add water vapor to the feed gas in an amount between 1 and 20 and, more preferably, between 2 and 15 by molar ratio based on methacrolein. The addition of water can promote the desorption of methacrylic acid from the surface of the catalyst and control the temperature distribution in the catalyst layer.

The feed gas to be supplied may further contain other inert gas, for example, nitrogen, carbon dioxide, saturated hydrocarbon or the like. The gaseous reaction products containing methacrolein obtained by catalytic oxidation of isobutylene or tertiary butanol can be used as they are as the feed gas.

The reaction temperature for practising the process of this invention is preferably between 200°-380° C. and, more preferably, 250°-350° C.

The amount of the feed gas to be supplied is preferably between 100 and 6000 $hr^{-1}$ and, more preferably, between 500 and 3600 $hr^{-1}$ in the space velocity (SV) based on the NTP standard. Since the increase in the space velocity (SV) has no substantial effect on the results of the reaction where the catalyst of this invention is employed, the reaction can be conducted at a high space velocity.

While the reaction of this invention can be effected at a pressure either above or below the atmospheric pressure, it is suitably effected generally at a pressure near the atmospheric pressure. The preferrd pressure for the reaction in this invention lies between 1 and 5 atm.

The reaction of this invention can be effected in any desired type of reactor such as of a fixed bed, a fluidized bed or a moving bed type.

In the following examples, no particular references are made to the details of oxygen in the catalyst composition since they are determined in accordance with the atomic ratio and valency of other elements.

The conversion of methacrolein, the yield of methacrylic acid and the selectivity to methacrylic acid are defined as follows:

Conversion of methacrolein (%) =

$$\frac{\text{methacrolein reacted (mol)}}{\text{methacrolein supplied (mol)}} \times 100$$

Yield of methacrylic acid (%) =

$$\frac{\text{methacrylic acid resulted (mol)}}{\text{methacrolein supplied (mol)}} \times 100$$

Selectivity to methacrylic acid (%) =

$$\frac{\text{yield of methacrylic acid}}{\text{conversion of methacrolein}} \times 100$$

EXAMPLE 1

100 g of molybdenum trioxide, 6.3 g of vanadium pentoxide, 3.0 g of copper phosphate, 2.1 g of tin oxide, and 6.4 g of orthophosphoric acid were dispersed or dissolved into 1000 ml of deionized water. The resultant mixture was boiled and refluxed with stirring for about 6 hours to produce a clear orange red solution. After removing a slight amount of insoluble contents, it was evaporated to dryness on a hot bath. The dried products thus obtained (catalyst) had a composition: $Mo_{10}V_1Cu_{0.3}Sn_{0.2}P_1$ and were confirmed to be a heteropoly-acid by the observation of diffraction peaks at $2\theta = 8.0°$, 8.9°, 9.3° and the like through X-ray diffraction. It was ground to 24–48 mesh and then charged into a tubular reactor made of Pyrex glass of 18 mm in inside diameter and the reactor was immersed in a fluidized bath. The feed gas of a composition wherein methacrolein:oxygen:nitrogen:water vapour=1:4:16:10 (in molar ratio) was caused to pass through the tubular reactor at $SV=1600$ $hr^{-1}$ (NTP standard) and subjected to oxidation reaction at a reaction temperature of 320° C. for 120 days. The results are shown in Table 1.

After the reaction of 120 days, X-ray diffraction analysis of the catalyst was made and it is confirmed that the molybdenum trioxide was not formed and the structure of the catalyst was not changed.

EXAMPLES 2-14

2.1 g of tin oxide in Example 1 was replaced in each of the examples with 3.7 g of thorium oxide, 1.4 g of germanium oxide, 1.0 g of nickel oxide, 1.1 g of iron oxide, 1.1 g of tricobalt tetroxide, 0.56 g of magnesium oxide, 1.1 g of zinc oxide, 1.1 g of titanium oxide, 3.2 g of trilead tetroxide, 3.4 g of rhenium heptoxide, 1.7 g of zirconium oxide, 1.4 g of chromium trioxide and 2.0 g of antimony trioxide respectively and dried products having compositions as shown in Table 1 were obtained. The dried products thus obtained were confirmed to be a heteropoly-acid by the observation of diffraction peaks at $2\theta=8.0°$, 8.9°, 9.3° and the like through X-ray diffraction.

A series of continuous reactions were conducted using the above catalysts under the same reaction conditions as in Example 1. The results are as shown in Table 1.

After the reaction of 30 days, X-ray diffraction analysis of the catalysts was made and it is confirmed that the structure of the catalysts was not changed.

TABLE 1

| Example | Catalyst Composition | Reaction time (days) | Reaction temperature (°C.) | Conversion of methacrolein (%) | Yield of methacrylic acid (%) | Selectivity to methacrylic acid (%) |
| --- | --- | --- | --- | --- | --- | --- |
| 1 | $Mo_{10}V_1Cu_{0.3}Sn_{0.2}P_1$ | 1 | 320 | 87.0 | 70.4 | 80.9 |
|  |  | 120 | 320 | 88.9 | 70.2 | 79.0 |
| 2 | $Mo_{10}V_1Cu_{0.3}Th_{0.2}P_1$ | 1 | 320 | 90.0 | 69.4 | 77.1 |
|  |  | 30 | 320 | 90.5 | 69.7 | 77.0 |
| 3 | $Mo_{10}V_1Cu_{0.3}Ge_{0.2}P_1$ | 1 | 320 | 93.9 | 70.4 | 75.0 |
|  |  | 30 | 320 | 94.5 | 71.3 | 75.5 |
| 4 | $Mo_{10}V_1Cu_{0.3}Ni_{0.2}P_1$ | 1 | 320 | 93.0 | 69.6 | 74.8 |
|  |  | 30 | 320 | 93.5 | 69.7 | 74.5 |
| 5 | $Mo_{10}V_1Cu_{0.3}Fe_{0.2}P_1$ | 1 | 315 | 95.1 | 71.3 | 75.0 |
|  |  | 30 | 315 | 95.0 | 71.5 | 75.3 |
| 6 | $Mo_{10}V_1Cu_{0.3}Co_{0.2}P_1$ | 1 | 312 | 92.6 | 70.5 | 76.2 |
|  |  | 30 | 312 | 93.2 | 70.8 | 76.0 |
| 7 | $Mo_{10}V_1Cu_{0.3}Mg_{0.2}P_1$ | 1 | 320 | 88.5 | 66.5 | 75.1 |
|  |  | 30 | 320 | 89.7 | 68.2 | 76.0 |
| 8 | $Mo_{10}V_1Cu_{0.3}Zn_{0.2}P_1$ | 1 | 320 | 85.0 | 68.0 | 80.0 |
|  |  | 30 | 320 | 85.5 | 68.2 | 79.8 |
| 9 | $Mo_{10}V_1Cu_{0.3}Ti_{0.2}P_1$ | 1 | 330 | 89.3 | 65.9 | 74.1 |
|  |  | 30 | 330 | 89.5 | 66.7 | 74.5 |
| 10 | $Mo_{10}V_1Cu_{0.3}Pb_{0.2}P_1$ | 1 | 330 | 87.0 | 66.6 | 76.5 |
|  |  | 30 | 330 | 87.2 | 66.7 | 76.5 |
| 11 | $Mo_{10}V_1Cu_{0.3}Re_{0.2}P_1$ | 1 | 320 | 90.5 | 72.9 | 80.5 |
|  |  | 30 | 320 | 90.8 | 73.1 | 80.5 |
| 12 | $Mo_{10}V_1Cu_{0.3}Zr_{0.2}P_1$ | 1 | 317 | 93.6 | 68.3 | 73.0 |
|  |  | 30 | 317 | 94.0 | 68.2 | 72.5 |
| 13 | $Mo_{10}V_1Cu_{0.3}Cr_{0.2}P_1$ | 1 | 320 | 91.0 | 64.6 | 71.0 |
|  |  | 30 | 320 | 91.5 | 64.5 | 70.5 |
| 14 | $Mo_{10}V_1Cu_{0.3}Sb_{0.2}P_1$ | 1 | 330 | 87.5 | 67.5 | 77.1 |
|  |  | 30 | 330 | 87.3 | 67.2 | 77.0 |

EXAMPLES 15-18

The dried products as shown in Table 2 were prepared as in Example 1 and were confirmed to be a heteropoly-acid by X-ray diffraction analysis.

The continuous reactions were conducted using the above catalysts in the same reaction conditions as in Example 1. The results are shown in Table 2.

After the reaction of 30 days, X-ray diffraction analysis of the catalysts was made and it is confirmed that the structure of the catalysts was not changed.

TABLE 2

| Example | Catalyst Composition | Reaction time (days) | Reaction Temperature (°C.) | Conversion of methacrolein (%) | Yield of methacrylic acid (%) | Selectivity to methacrylic acid (%) |
| --- | --- | --- | --- | --- | --- | --- |
| 15 | $Mo_{10}V_1Cu_{0.2}Th_{0.1}Sn_{0.1}P_1$ | 1 | 320 | 93.5 | 71.2 | 76.1 |
|  |  | 30 | 320 | 93.7 | 71.2 | 76.0 |
| 16 | $Mo_{10}V_1Cu_{0.2}Ge_{0.1}Ni_{0.1}P_1$ | 1 | 320 | 90.8 | 70.0 | 77.1 |
|  |  | 30 | 320 | 91.5 | 70.3 | 76.8 |
| 17 | $Mo_{10}V_1Cu_{0.2}Mg_{0.1}Th_{0.1}P_1$ | 1 | 320 | 94.5 | 70.4 | 74.5 |
|  |  | 30 | 320 | 94.7 | 70.6 | 74.5 |
| 18 | $Mo_{10}V_1Cu_{0.2}Sn_{0.1}Zr_{0.1}P_1$ | 1 | 320 | 89.5 | 72.5 | 81.0 |
|  |  | 30 | 320 | 89.6 | 72.8 | 81.2 |

EXAMPLES 19-24

The dried products as shown in Table 3 were prepared as in Example 1 and were confirmed to be a heteropoly-acid by X-ray diffraction analysis.

The continuous reactions were conducted using the above catalysts in the same reaction conditions as in Example 1. The results are shown in Table 3.

After the reaction of 30 days, X-ray diffraction analysis of the catalysts was made and it is confirmed that the structure of the catalysts was not changed.

EXAMPLES 25-26

With use of the catalyst of Example 5 the oxidation of methacrolein was carried out in a similar manner as in Example 1 except that the space velocity (SV) was changed. The results are shown in Table 5. These results show that the increase in the space velocity (SV) has no substantial effect on the results of the reaction.

TABLE 5

| Example | Catalyst Composition | SV (hr$^{-1}$) | Reaction temperature (°C.) | Conversion of methacrolein (%) | Yield of methacrylic acid (%) | Selectivity to methacrylic acid (%) |
|---|---|---|---|---|---|---|
| 25 | $Mo_{10}V_1Cu_{0.3}Fe_{0.2}P_1$ | 800 | 290 | 94.5 | 71.8 | 76.0 |
| 26 | $Mo_{10}V_1Cu_{0.3}Fe_{0.2}P_1$ | 3600 | 335 | 94.7 | 71.0 | 75.0 |

TABLE 3

| Example | Catalyst Composition | Reaction time (days) | Reaction temperature (°C.) | Conversion of methacrolein (%) | Yield of methacrylic acid (%) | Selectivity to methacrylic acid (%) |
|---|---|---|---|---|---|---|
| 19 | $Mo_{10}V_2Cu_{0.3}Sn_{0.1}P_1$ | 1 | 340 | 85.6 | 64.5 | 75.3 |
|  |  | 30 | 340 | 85.7 | 64.3 | 75.0 |
| 20 | $Mo_{10}V_1Cu_{0.2}Sn_{0.1}P_{1.5}$ | 1 | 330 | 88.1 | 67.4 | 76.5 |
|  |  | 30 | 330 | 89.1 | 68.2 | 76.5 |
| 21 | $Mo_{10}V_1Cu_{1.0}Sn_{0.2}P_1$ | 1 | 300 | 88.5 | 66.4 | 75.0 |
|  |  | 30 | 300 | 88.0 | 65.8 | 74.8 |
| 22 | $Mo_{10}V_1Cu_{0.05}Ni_{0.05}P_1$ | 1 | 330 | 89.7 | 69.2 | 77.2 |
|  |  | 30 | 330 | 90.0 | 69.4 | 77.1 |
| 23 | $Mo_{10}V_1Cu_{0.1}Sn_{0.03}P_1$ | 1 | 320 | 86.5 | 69.0 | 79.8 |
|  |  | 30 | 320 | 87.0 | 69.3 | 79.6 |
| 24 | $Mo_{10}V_{0.7}Cu_{0.2}Sn_{0.1}P_1$ | 1 | 330 | 87.1 | 65.0 | 74.6 |
|  |  | 30 | 330 | 87.9 | 65.5 | 74.6 |

COMPARISON EXAMPLE 1

Dried products having a composition, $Mo_{10}V_1Cu_{0.3}P_1$ were obtained in the same procedures as in Example 1 but with no addition of 2.1 g of tin oxide and a similar continuous reaction was conducted using the above catalyst. The results are as shown in Table 4.

COMPARISON EXAMPLE 2

A 28% aqueous ammonia solution was added to the clear orange red solution obtained in Example 1 (pH=1.0) to adjust the pH value to 5.3. After evaporating the solution to dryness, the dried products were ground to 24-48 mesh and calcined in air at 380° C. for 8 hours. The catalyst prepared had a composition: $(NH_4)_{1.5}Mo_{10}V_1Cu_{0.3}Sn_{0.2}P_1$ and the formation of an ammonium salt of heteropoly-acid was confirmed from X-ray diffraction and IR absorption spectrum. A similar continuous reaction was conducted using the above catalyst. The results are shown in Table 4.

What is claimed is:

1. A process for producing methacrylic acid by oxidizing methacrolein with molecular oxygen or molecular oxygen-containing gas in the vapor phase characterized by the use of a catalyst having a heteropoly-acid structure and the general formula:

$$Mo_aV_bP_cCu_dX_eO_f$$

wherein Mo, V, P, Cu and O represent respectively molybdenum, vanadium, phosphorus, copper and oxygen, X represents one or more elements selected from the group consisting of tin, thorium, germanium, nickel, iron, cobalt, magnesium, zinc, titanium, lead, rhenium, zirconium, and chromium and a, b, c, d, e and f represent the atomic ratio of the elements where,
  a is 10
  b is a number of 3 or less than 3 excluding 0,
  c is a number of 0.5 to 3,
  d is a number of 3 or less than 3 excluding 0,
  e is a number of 3 or less than 3 excluding 0,
  f is a number determined depending on the valency and atomic ratio of the other elements in the formula.

TABLE 4

| Comparison Example | Catalyst Composition | Reaction time (days) | Reaction Temperature (°C.) | Conversion of methacrolein (%) | Yield of methacrylic acid (%) | Selectivity to methacrylic acid (%) |
|---|---|---|---|---|---|---|
| 1 | $Mo_{10}V_1Cu_{0.3}P_1$ | 1 | 320 | 88.7 | 62.0 | 70.4 |
|  |  | 30 | 320 | 88.0 | 61.6 | 70.0 |
| 2 | $(NH_4)_{1.5}Mo_{10}V_1Cu_{0.3}Sn_{0.2}P_1$ | 1 | 320 | 87.5 | 71.8 | 82.1 |
|  |  | 15 | 320 | 71.8 | 53.9 | 75.0 |

2. The process of claim 1, wherein a is 10, b is a number of 0.5 to 2, c is a number of 0.5 to 2, d is a number of 0.01 to 1 and e is a number of 0.01 to 0.5.

3. The process of claim 1, wherein X represents one or more elements selected from the group consisting of tin, thorium, germanium, nickel, iron, cobalt, titanium and zirconium.

4. The process of claim 1, wherein the reaction temperature is between 200° and 380° C.

5. The process of claim 1, wherein the reaction is conducted in the presence of water vapour.

* * * * *